United States Patent [19]

Stucky et al.

[11] Patent Number: 5,446,159
[45] Date of Patent: Aug. 29, 1995

[54] PROCESS FOR PREPARING IMIDAZOPYRIDINE DERIVATIVES

[75] Inventors: Gerhard Stucky; René Imwinkelried, both of Brig-Glis, Switzerland

[73] Assignee: Lonza, Ltd., Gampel/Valais, Switzerland

[21] Appl. No.: 308,431

[22] Filed: Sep. 19, 1994

[30] Foreign Application Priority Data

Sep. 17, 1993 [CH] Switzerland .................. 2815/93

[51] Int. Cl.$^6$ .......................................... C07D 471/02
[52] U.S. Cl. .......................................... 546/118
[58] Field of Search .......................................... 546/118

[56] References Cited

U.S. PATENT DOCUMENTS

| | | | |
|---|---|---|---|
| 4,097,525 | 6/1978 | Kraska | 260/564 |
| 5,066,654 | 11/1991 | Taylor, Jr. et al. | 514/256 |
| 5,240,938 | 8/1993 | Greenlee et al. | 514/303 |

FOREIGN PATENT DOCUMENTS

| | | |
|---|---|---|
| 0130461 | 1/1985 | European Pat. Off. . |
| 0385850 | 12/1990 | European Pat. Off. . |
| 0510813 | 10/1992 | European Pat. Off. . |

OTHER PUBLICATIONS

Katritzky A. R. and Yousaf, T. I. Cau. J. Chem. 64 pp. 2087–2093 (1986).
WO93/23399 International Published Application Nov. 25, 1993.
Mantlo; N.B. et al., J. Med. Chem., (1991), 34, pp. 2919 to 2922.
Bader, H. et al., J. Chem. Soc., (1950), p. 2780.

*Primary Examiner*—C. Warren Ivy
*Assistant Examiner*—Evelyn Huang
*Attorney, Agent, or Firm*—Fisher, Christen & Sabol

[57] ABSTRACT

A process for preparing imidazopyridines of the general formula:

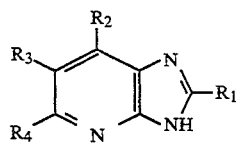

I wherein $R_1$ is an alkyl, cycloalkyl, aryl or aralkyl group or is a heterocyclic radical, $R_2$ and $R_4$ are identical or different and are hydrogen, a hydroxy, a cyano, alkyl, cycloalkyl, aryl or aralkyl group or are an alkanoyl or an alkoxy-carbonyl group, and $R_3$ is hydrogen, an alkyl, aryl or aralkyl group or a halogen atom. In the key step of the process, an amidine of the formula:

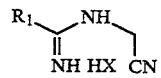

V is cyclized with a 1,3-dicarbonyl compound of the general formula:

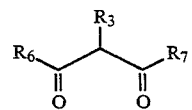

VI.

The imidazopyridines are valuable intermediates for the preparation of angiotensin II antagonists.

13 Claims, No Drawings

PROCESS FOR PREPARING IMIDAZOPYRIDINE DERIVATIVES

BACKGROUND OF THE INVENTION

1. Field of the Invention

The invention relates to a new process for preparing imidazopyridine derivatives of the general formula:

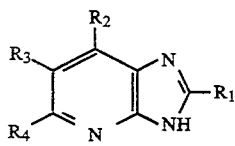

I wherein $R_1$ is an alkyl, cycloalkyl, aryl or aralkyl group or is a heterocyclic radical, $R_2$ and $R_4$ are identical or different and are hydrogen, a hydroxy, a cyano, alkyl, cycloalkyl, aryl or aralkyl group or are an alkanoyl or an alkoxy-carbonyl group, and $R_3$ is hydrogen, an alkyl, aryl or aralkyl group or a halogen atom.

2. Background Art

In *J. Med. Chem.*, (1991), 34, 2919 to 2922, it is described that the imidazopyridines of the general formula I can be obtained by reduction of 2-amino-3-nitropyridines and subsequent condensation with an appropriate aliphatic carboxylic acid. However, the preparation of the starting materials for the 2-amino-3-nitropyridines is difficult, since the nitration of the corresponding aminopyridines does not proceed regioselectively.

BROAD DESCRIPTION OF THE INVENTION

An object of the invention is to provide a process which provides a simple route, usable on a large scale, to the imidazopyridines of the general formula I. Other objects and advantages of the invention are set out herein or are obvious herefrom to one skilled in the art.

The objects and advantages of the invention are achieved by the process of the invention.

The invention involves a process for preparing. imidazopyridine derivatives of the general formula:

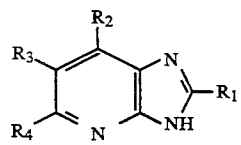

I wherein $R_1$ is an alkyl, cycloalkyl, aryl or aralkyl group or is a heterocyclic radical, $R_2$ and $R_4$ are identical or different and are hydrogen, a hydroxy, a cyano, alkyl, cycloalkyl, aryl or aralkyl group or are an alkanoyl or an alkoxy-carbonyl group, and $R_3$ is hydrogen, an alkyl, aryl or aralkyl group or a halogen atom. The process includes reacting a nitrile of the general formula:

$$R_1 CN \qquad\qquad II$$

wherein $R_1$ is as defined above, with a thiol of the general formula:

$$R_5 SH \qquad\qquad III$$

wherein $R_5$ is alkyl, aryl or aralkyl, in the presence of a hydrogen halide to give a thioimidate hydrohalide of the general formula:

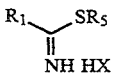

IV wherein $R_1$ and $R_5$ are as defined above and X is a halogen atom. The thioimidate hydrohalide of the general formula IV is allowed to react with aminoacetonitrile to give the amidine of the general formula:

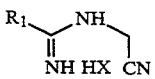

V wherein $R_1$ and X are as defined above. Finally, the amidine of the general formula V is cyclized in the presence of a base with a 1,3-dicarbonyl compound of the general formula:

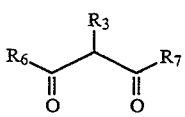

VI wherein $R_3$ is as defined above and $R_6$ and $R_7$ are identical or different and are hydrogen or alkyl, cyano, cycloalkyl, alkonoyl, aryl, aralkyl, alkoxy or alkoxycarbonyl, to give the final product of the general formula I.

Preferably the thioimidate hydrohalide of the general formula IV is not isolated. Preferably the reaction to give the thioimidate hydrohalide of the general formula IV is carried out in the presence of hydrogen chloride and at reaction temperatures between 0° C. and room temperature, with or without the addition of an inert solvent. Preferably the reaction to give the amidine of the general formula V is caried out at temperatures between 0° C. and the reflux temperature of the respective solvent. Preferably the base used for the cyclization is an inorganic or organic base. Preferably the base used for the cyclization is an alkali metal alkoxide, or an alkali metal hydroxide in a lower aliphatic alcohol. Preferably the cyclization is carried out at temperatures between 0° C. and reflux temperature, in the presence or absence of an inert solvent. Preferably the aminoacetonitrile is liberated from a salt of aminoacetonitrile by means of a base.

The compounds produced by the invention process are used as intermediates for the preparation of angiotension II antagonists. [*J. Med. Chem.*, (1991), 34, 2919 to 2922].

DETAILED DESCRIPTION OF THE INVENTION

The terms used for the individual radicals $R_1$ to $R_7$ and X have the following meanings.

The term alkyl group means a straight-chain or branched alkyl group having advantageously from 1 to 6 carbon atoms, preferably having from 1 to 4 carbon atoms. Examples of the alkyl group are methyl, ethyl, n-propyl, i-propyl, n-butyl and t-butyl. The term cycloalkyl group advantageously means a $C_3$–$C_6$-cycloalkyl group, such as, cyclopropyl, cyclobutyl, cyclopentyl or cyclohexyl. The term aryl group includes carbocyclic aromatic groups, advantageously phenyl or naphthyl. The term aralkyl group denotes an aryl-substituted alkyl group, advantageously a phenyl-substituted $C_1$–$C_6$-alkyl group, in particular benzyl. The term alkanoyl group advantageously means a $(C_1-C_6)$-alkanoyl group, preferably acetyl. The term alkoxy group is advantageously a $(C_1-C_6)$-alkoxy group, preferably methoxy or ethoxy.

The term heterocyclic radical advantageously means a heterocycle having a 5-membered or 6-membered ring and having nitrogen and/or oxygen and/or sulfur as the heteroatom. Likewise, condensed ring systems of heterocycles with one another or of heterocycles with carbocyclic systems are included under the specified term. Examples of heterocycles having a 5-membered ring are the furans, the thiophenes, the pyrroles, the indoles, the pyrazoles, the imidazoles, the oxazoles, isoxazoles, the thiazoles, and the triazoles. Examples of heterocycles having a 6-membered ring are the pyridines, the quinolines, the isoquinolines, the acridines, the pyridazines, the pyrimidines, the pyrazines, the phenazines, the purines, and the pteridines.

Halogen is fluorine, chlorine, bromine or iodine; the preferred halogen is chlorine.

The specified groups, in particular the cyclic radicals, can in each case be monosubstituted or polysubstituted. Suitable radicals are, for example, halo, nitro, amino, alkylamino, dialkylamino, hydroxy, alkoxy, alkyl or alkanoyl. The above explanations of the term meanings apply to these radicals.

In the first stage of the process of the invention, a nitrile of the general formula:

$R_1CN$  II wherein R1 is as defined above, is reacted with a thiol of the general formula:

$R_5SH$  III wherein $R_5$ is alkyl, aryl or aralkyl, in the presence of a hydrogen halide to give a thioimidate hydrohalide of the general formula:

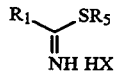

IV wherein $R_1$ and $R_5$ are as defined above and X is a halogen atom. This first stage has essentially been described by Bader et al. in *J. Chem. Soc.*, (1950), 2780.

The nitrile of the general formula II which is used is advantageously acetonitrile, propionitrile, butyronitrile or valeronitrile. The particularly preferred nitrile of the general formula II is propionitrile. Furthermore, benzyl mercaptan is preferably used as a thiol of the general formula III and hydrogen chloride is preferably used as hydrogen halide. In principle, the nitrile used can function as solvent. However, in general, use is additionally made of an inert solvent, for example, dioxane, tetrahydrofuran, ether, a halogenated hydrocarbon, such as, methylene chloride, or an aromatic hydrocarbon, such as, toluene.

It has been found that the reaction in the first stage is advantageously carried out at temperatures between 0° C. and room temperature. The reaction time essentially depends on the amount of hydrogen halide. The best results are obtained in the range of from 2 to 3 equivalents of hydrogen halide per equivalent of thiol of the general formula III.

The resulting thioimidate of the general formula IV can be isolated in a manner known to those skilled in the art, but it is preferably directly reacted further with aminoacetonitrile to give the amidine of the general formula:

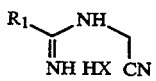

V wherein $R_1$ and X are as defined above. The aminoacetonitrile is, in each case, advantageously liberated directly prior to the reaction from a corresponding aminoacetonitrile salt, such as, the hydrochloride or the hydrosulfate, by reaction of the corresponding aminoacetonitrile salt with a base, for example, ammonia. The reaction is usually carried out in the solvent of the preliminary (first) stage. The reaction temperature is advantageously between 0° C. and the reflux temperature of the respective solvent.

The resultant amidine of the general formula V can, after the reaction is complete, be taken from the reaction mixture in a manner known to those skilled in the art, for example, by filtration, in the case of the amidine of the general formula V having $R_1$ being ethyl and X being Cl.

In the last stage, the amidine of the general formula V is cyclized in the presence of a base with a 1,3-dicarbonyl compound of the general formula:

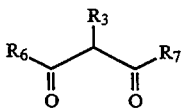

VI wherein $R_3$ is as defined above and $R_6$ and $R_7$ are identical or different and are hydrogen, alkyl, cyano, cycloalkyl, alkonoyl, aryl, aralkyl, alkoxy or alkoxycarbonyl, to give the final product.

Suitable 1,3-dicarbonyl compounds having $R_6$ and $R_7$ being akyl are the alkanediones, such as, 2,4-pentanedione (acetylacetone), 3,5-heptanedione, 4,6-nonanedione or, with $R_3$ being methyl, 3-methyl-2,4-pentanedione (2-methylacetylacetone). Representatives of the 1,3-dicarbonyl compounds having $R_6$ being alkyl and $R_7$ being alkoxy are the alkanoylacetic esters, such as, methyl acetoacetate or ethyl acetoacetate. The malonic esters having $R_6$ and $R_7$ being alkoxy are also advantageously used; examples are methyl malonate and ethyl malonate. Suitable compounds of the general formula VI having $R_6$ and $R_7$ being hydrogen are malondialdehyde or the 2-substituted malondialdehydes. Further suitable representatives of the general formula VI having $R_6$ and $R_7$ being alkoxycarbonyl are dimethyl 2,4-dioxopentanedioate or diethyl 2,4-dioxopentanedioate having $R_6$ and $R_7$ being methoxycarbonyl and ethoxycarbonyl.

The bases used can be inorganic or organic bases. Advantageously, as the organic base of the cyclization, use is made of an alkali metal alkoxide, such as, sodium or potassium ethoxide, sodium/potassium methoxide or potassium t-butoxide in the corresponding alcohol, or a trialkylamine, such as, triethylamine. As the inorganic base, use is advantageously made of alkali metal hydroxides in a lower aliphatic alcohol, such as, NaOH or KOH in methanol or water, or else alkali metal or alkaline earth metal carbonates or hydrogen carbonates. The selection of solvent is not especially critical. Good results can be obtained with lower aliphataic alcohols, such as, methanol or ethanol, but also with aromatic hydrocarbons, such as, toluene.

The reaction advantageously proceeds between room temperature and the reflux temperature of the respective solvent, preferably between 50° C. and the reflux temperature of the solvent.

After the reaction is complete, the imidazopyridine can be separated off from the reaction mixture in a conventional manner.

EXAMPLE 1

(a) Process for preparing S-benzylpropionthioamide.HCl 43 g (1.2 mol; 3eq) of HCl gas was passed at 10° C. into a solution of 50.2 g (0.4 mol) of benzyl mercaptan and 24.2 g (0.44 mol) of propionitrile in 100 ml of dioxane. After passing-in of the gas is complete (about 1 hour), the mixture was warmed to room temperaure. After 2.5 hours, a part of the dioxane and excess HCl were drawn off by means of a vacuum, with the product precipitating. The precipitated product was filtered off, washed with a little ether and dried in vacuo. This operation gave 82.1 g of white title product (yield 95 percent). Other data concerning the product is:

$^1$H-NMR: (CDCl$_3$, 300 MHz) δ1.4 (t, 3H) 2.95 (q, 2H) 4.25 (s, 2H) 7.3–7.5 (m, 5H) 12.2 (br. s, 1H0 13.1 (br. s, 1H)

(b) Process for preparing 1-iminopropylamino)-acetonitrile.HCl

A suspension of 81.5 g (0.38 mol) of the product from 1(a) in 300 ml of dioxane was cooled to about 10° C. and admixed with 23.8 g (0.42 mol) of aminoacetonitrile (liberated from the aminoacetonitrile hydrochloride using ammonia). After two hours at this temperature, the product was filtered off, washed with ether and dried in vacuo. This operation gave 52.2 g of white title product (yield 93 percent). The product had a melting point of 92° to 93° C. Other data concerning the product was:

$^1$H-NMR: (DMSO, 400 MHz) δ1.2 (t, 3H) 2.5 (q, 2H) 4.6 (s, 2H) 9.6 (s, 1H) 10.0 (s, 1H) 10.6 (s, 1H)

(c) Process for preparing (1-aminopropylamino)-acetonitrile.HCl 7.3 g (0.2 mol) of HCl was passed at 10° C. into a solution of 12.4 g (0.1 mol) of benzylmercaptan and 6.1 g (0.11 mol) of propionitrile in 25 ml of dioxane. After passing-in of the gas was complete, the mixture was stirred for 17 hours at room temperature. The excess HCl was drawn off by means of a vacuum. To the resultant suspension, 6.16 g (0.11 mol) of aminoacetonitrile (liberated from the hydrochloride using ammonia) was added dropwise at room temperature and the mixture was stirred for two hours at this temperature. The resultant solid was filtered off, washed with ether and dried in vacuo. This operation gave 11 g of white title product (yield based on propionitrile: 75 percent).

(d) Process for preparing 2-ethyl-5,7-dimethyl-3H-imidazo[4,5-b]pyridine 150 ml of a 1.6M sodium ethoxide solution in ethanol (corresponding to 0.24 mol of NaOEt) was added dropwise at 0° C. to a solution of 35.4 g (0.24 mol) of the product from 1(c) in 150 ml of ethanol. 240 g (2.4 mol; 10 eq) of acetylacetone was subsequently added, and the reaction mixture was slowly heated to 130° C. The water and the ethanol were thereby distilled off. After half an hour at reflux temperature, the mixture was cooled to room temperature, admixed with 500 ml of water and 500 ml of ethyl acetate, and the phases were separated. The organic phase was dried with MgSO$_4$ and evaporated on a rotary evaporator. The residue obtained was recrystallized from ethyl acetate. This operation gave 25.5 g (60%) of pale yellowish title product. The melting point of the product was 148.8° to 150.4° C. Other data concerning the product was:

$^1$H-NMR: (400 MHz in CD$_3$OD) δ1.4 (t, 3H) 2.55 (s, 6H 2.9 (q, 2H) 6.9 (S, 1H)

What is claimed is:

1. Process for preparing an imidazopyridine derivative of formula:

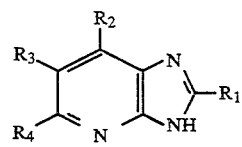

wherein R$_1$ is an alkyl, cycloalkyl, aryl or aralkyl group or is a heterocyclic radical, R$_2$ and R$_4$ are identical or different and are hydrogen, a hydroxy, a cyano, alkyl, cycloalkyl, aryl or aralkyl group or are an alkanoyl or an alkoxy-carbonyl group, and R$_3$ is hydrogen, an alkyl, aryl or aralkyl group or a halogen atom, comprising reacting a nitrile of formula:

   II wherein R$_1$ is as defined above, with a thiol of formula:

   III wherein R$_5$ is alkyl, aryl or aralkyl, in the presence of a hydrogen halide to give a thioimidate hydrohalide of formula:

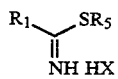   IV wherein R$_1$ and R$_5$ are as defined above and X is a halogen atom, reacting the thioimidate hydrohalide of formula IV with aminoacetonitrile to give an amidine of formula:

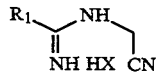   V wherein R$_1$ and X are as defined above, and finally cyclizing the amidine of formula V in the presence of a base with a 1,3-dicarbonyl compound of formula:

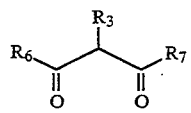   VI wherein R$_3$ is as defined above and R$_6$ and R$_7$ are identical or different and are hydrogen or alkyl, cyano, cycloalkyl, alkanoyl, aryl, aralkyl, alkoxy or alkoxycarbonyl, to give the final product of formula I.

2. The process according to claim 1 wherein the thioimidate hydrohalide of formula IV is not isolated.

3. The process according to claim 1 wherein the reaction to give the thioimidate hydrohalide of formua IV is carried out in the presence of hydrogen chloride and at a reaction temperature between 0° C. and room temperature, with or without the addition of an inert solvent.

4. The process according to claim 3 wherein the reaction to give the amidine of formula V is carried out at a temperature between 0° C. and the reflux temperature of the respective solvent.

5. The process according to claim 4 wherein the base used for the cyclization is an inorganic base or an organic base.

6. The process according to claim 5 wherein the base used for the cyclization is an alkali metal alkoxide, or an alkali metal hydroxide in a lower aliphatic alcohol.

7. The process according to claim 6 wherein the cyclization is carried out at a temperature between 0° C. and reflux temperature, in the presence or absence of an inert solvent.

8. The process according to claim 7 wherein the aminoacetonitrile is liberated from a salt of aminoacetonitrile by means of a base.

9. The process according to claim 1 wherein the reaction to give the amidine of formula V is carried out at a temperature between 0° C. and the reflux temperature of the respective solvent.

10. The process according to claim 1 wherein the base used for the cyclization is an inorganic base or an organic base.

11. The process according to claim 10 wherein the base used for the cyclization is an alkali metal alkoxide, or an alkali metal hydroxide in a lower aliphatic alcohol.

12. The process according to claim 1 wherein the cyclization is carried out at a temperature between 0° C. and reflux temperature, in the presence or absence of an inert solvent.

13. The process according to claim 1 wherein the aminoacetonitrile is liberated from a salt of aminoacetonitrile by means of a base.

* * * * *